(12) United States Patent
Russell

(10) Patent No.: US 8,109,922 B2
(45) Date of Patent: *Feb. 7, 2012

(54) ORIFICE DEVICE HAVING MULTIPLE CHANNELS AND MULTIPLE LAYERS FOR DRUG DELIVERY

(75) Inventor: Scott M. Russell, San Jose, CA (US)

(73) Assignee: Cordis Corporation, Miami Lakes, FL (US)

( * ) Notice: Subject to any disclaimer, the term of this patent is extended or adjusted under 35 U.S.C. 154(b) by 858 days.

This patent is subject to a terminal disclaimer.

(21) Appl. No.: 10/855,141

(22) Filed: May 27, 2004

(65) Prior Publication Data

US 2004/0267241 A1    Dec. 30, 2004

Related U.S. Application Data

(63) Continuation-in-part of application No. 10/460,460, filed on Jun. 12, 2003, now Pat. No. 7,678,103.

(51) Int. Cl.
*A61K 9/22* (2006.01)
(52) U.S. Cl. .................... 604/891.1; 604/892.1
(58) Field of Classification Search ............... 604/93.01, 604/118, 246, 247, 264, 523, 537, 890.1, 604/891.1, 891.2, 892.1, 288.01, 288.04; 138/37, 42
See application file for complete search history.

(56) References Cited

U.S. PATENT DOCUMENTS

| | | | | |
|---|---|---|---|---|
| 2,146,823 A | * | 2/1939 | Karmazin | ........................ 138/42 |
| 2,323,115 A | | 6/1943 | Bryant | |
| 2,532,019 A | * | 11/1950 | Goldberg | ........................ 138/43 |
| 3,777,343 A | * | 12/1973 | D'Onofrio | ............... 29/890.036 |
| 3,951,147 A | | 4/1976 | Tucker et al. | |
| 3,998,244 A | | 12/1976 | Bentley | |
| 4,176,683 A | | 12/1979 | Leibinsohn | |
| 4,411,292 A | * | 10/1983 | Schiller | ........................ 138/42 |
| 4,455,144 A | | 6/1984 | Michaels | |
| 4,564,364 A | | 1/1986 | Zaffaroni et al. | |
| 4,634,434 A | | 1/1987 | Marino, Jr. et al. | |
| 4,969,884 A | | 11/1990 | Yum | |

(Continued)

FOREIGN PATENT DOCUMENTS

CH           435 557 A        5/1967

(Continued)

OTHER PUBLICATIONS

European Search Report EP 05253248 dated Oct. 25, 2005.

(Continued)

*Primary Examiner* — Kevin C Sirmons
*Assistant Examiner* — Laura Schell
(74) *Attorney, Agent, or Firm* — Louis J. Capezzuto (57) ABSTRACT

An orifice device for delivering one or more drugs includes an inner member having a proximal end and a distal end; and a plurality of windings helically wound around the inner member. Each winding defines a separate layer and each winding includes at least one wire helically wound around the inner member. The plurality of windings and the inner member define at least two separate channels for carrying one or more drugs therethrough. An inlet is at the proximal end of each of the plurality of windings and an outlet is at the distal end of the plurality of windings. At least one of the plurality of windings has a plurality of distinct wires helically wound in parallel around the inner member and at least one of the plurality of windings respectively.

29 Claims, 11 Drawing Sheets

U.S. PATENT DOCUMENTS

| | | |
|---|---|---|
| 5,122,128 A | 6/1992 | Cardinal et al. |
| 5,267,979 A | 12/1993 | Appling et al. |
| 5,318,558 A | 6/1994 | Linkwitz et al. |
| 5,495,963 A | 3/1996 | Miller et al. |
| 5,554,114 A | 9/1996 | Wallace et al. |
| 5,819,775 A | 10/1998 | Holloway |
| 5,855,713 A * | 1/1999 | Harvey .................. 156/153 |
| 5,985,305 A | 11/1999 | Peery et al. |
| 6,053,903 A | 4/2000 | Samson |
| 6,156,331 A | 12/2000 | Peery et al. |
| 6,248,093 B1 * | 6/2001 | Moberg .................. 604/131 |
| 6,261,584 B1 | 7/2001 | Peery et al. |
| 6,270,483 B1 | 8/2001 | Yamada et al. |
| 6,508,804 B2 * | 1/2003 | Sarge et al. .............. 604/524 |
| 6,524,302 B2 * | 2/2003 | Kelley .................... 604/523 |
| 6,524,305 B1 | 2/2003 | Peterson et al. |
| 6,736,796 B2 * | 5/2004 | Shekalim ................. 604/134 |
| 7,014,636 B2 | 3/2006 | Gilbert |
| 2003/0088236 A1 | 5/2003 | Johnson et al. |
| 2004/0193144 A1 * | 9/2004 | Krumme ................. 604/890.1 |
| 2004/0254565 A1 | 12/2004 | Russell |
| 2004/0267241 A1 | 12/2004 | Russell |

FOREIGN PATENT DOCUMENTS

| | | |
|---|---|---|
| DE | 19934445 A1 | 2/2001 |
| EP | 0 521 968 B1 | 10/1993 |
| EP | 0 935 976 B1 | 12/2003 |
| WO | WO 94/07562 A1 | 4/1994 |
| WO | WO 98/42317 A2 | 10/1998 |
| WO | WO 02/07810 A2 | 1/2002 |
| WO | WO 03/045352 A | 6/2003 |

OTHER PUBLICATIONS

European Search Report EP 05253247 dated Oct. 25, 2005.
European Search Report EP 04 25 3356 dated Oct. 4, 2004.

* cited by examiner

ORIFICE DEVICE HAVING MULTIPLE CHANNELS AND MULTIPLE LAYERS FOR DRUG DELIVERY

This is a continuation-in-part application of Ser. No. 10/460,460 filed Jun. 12, 2003, now U.S. Pat. No. 7,678,103, which is incorporated herein by reference.

FIELD AND BACKGROUND OF THE INVENTION

The present invention relates, in general, to drug delivery, and in particular, to a new and useful device for delivering drugs to the body of a patient at a very low fluid flow rate. The present invention also includes the method of manufacture of the novel drug delivery device.

Fluid delivery devices, and particularly, drug delivery devices are known. Additionally, it is also known within the fluid delivery or drug delivery field, that fluids, such as drugs, can be moved through helical flow paths. For example, U.S. Pat. No. 3,998,244 (Bentley) describes a drip irrigation valve with a helical flow path for the delivery of various agricultural liquids, such as fertilizers to be fed through an irrigation system. This particular system is useful for providing drip irrigation that conserves water, minimizes weed growth and facilitates the transport of the agricultural liquids through the irrigation system.

U.S. Pat. No. 4,176,683 (Leibinsohn) describes a flow regulator useful in apparatus designed for administering liquids to the body. The device is a presettable fluid flow regulator having an elongated sleeve of flexible material and a core within the sleeve having a helical recess of varying cross section carved or scored into the core. A ring on the outside of the sleeve has an internal diameter slightly less than the outer diameter of the sleeve and is used to squeeze the sleeve against the core to define a flow passage between the core and the sleeve. The volume of flow is determined by the longitudinal position of the ring along the sleeve.

U.S. Pat. No. 6,270,483 (Yamada et al.) describes a liquid discharge regulator and a liquid feeder that utilizes a liquid discharge regulator. The regulator has a channel spirally carved or formed on the surface of a passage forming member. The surface of the passage forming member is brought into close contact with the inner surface of a housing part wherein the channel functions as a liquid passage. The passage forming member is made of a plastic material by using injection molding manufacturing and mass production. The main purpose behind using the plastic material made exclusively through the injection molding process for the formation of the passage forming member is aimed at reducing manufacturing costs of the regulator.

U.S. Pat. No. 5,985,305 (Peery et al.) describes a back-diffusion regulating outlet consisting of a male threaded member in threaded relationship with a smooth interior surface of a reservoir thereby forming a helical flow path. As clearly shown, similar to the other prior art flow regulator devices, the regulating outlet consists of a solid core of material which serves as a male thread mating relationship with the smooth interior surface of the reservoir.

To date, there have been no fluid flow regulator devices, mechanisms or drug delivery devices using these type of mechanisms that can be provided or manufactured in an extremely efficient manner, easily and readily adapt configuration, and having extremely low cost of manufacturing.

SUMMARY OF THE INVENTION

The present invention is directed toward the field of drug delivery and relates to a novel orifice feature, mechanism or drug regulator device such as an orifice device. The present invention also relates to a drug delivery de mechanism and includes a novel implantable pump, a novel drug delivery device such as a drug delivery catheter or a novel implantable drug delivery device such as an implantable drug pump.

For purposes of this disclosure, the term "drug" means any type of molecules or compounds deliverable to a patient to include being deliverable as a fluid, slurry or fluid-like manner. The term "drug" is also defined as meaning any type of therapeutic agent or diagnostic agent which can include any type of medicament, pharmaceutical, chemical compounds, dyes, biological molecules to include tissue, cells, proteins, peptides, hormones, signaling molecules or nucleic acids such as DNA and RNA.

One embodiment of the present invention is an orifice device such as an orifice mechanism or drug dispenser regulator or regulator feature (all commonly referred to herein as "orifice device" or "orifice mechanism" or "orifice"). In accordance with the present invention, the orifice device is used to deliver a drug and comprises an inner member having a proximal end and a distal end and a winding helically wound around the inner member. The winding and the inner member define a first channel for carrying a drug therethrough (an active channel). An inlet is at the proximal end of the winding and an outlet is at the distal end of the winding.

Another embodiment of the present invention is a device for delivering a drug wherein the device comprises a body having a proximal end and a distal end and an opening in the distal end of the body. An orifice mechanism is included at the distal end of the body and is in fluid communication with the opening. The orifice mechanism comprises an inner member having a proximal end and a distal end and a winding helically wound around the inner member. The winding and the inner member define a first channel for carrying a drug therethrough (an active channel) and an inlet at the proximal end of the winding and an outlet at the proximal end of the winding.

In this embodiment according to the present invention, the novel device is a drug delivery device such as a drug delivery catheter or an infusion port device such as an intravenous (IV) port or IV fluid or drug delivery device.

Another embodiment of the present invention is a novel implantable device for delivering a drug wherein the device comprises a housing and a source of drug contained within the housing. An orifice mechanism is located at, on or within the housing and fluidly communicates with the source of drug. The orifice mechanism comprises an inner member having a proximal end and a distal end and a winding helically wound around the inner member. The winding and the inner member define a first channel for carrying the drug therethrough (an active channel) and an inlet at the proximal end of the winding and an outlet at the distal end of the winding. The drug is carried by the orifice mechanism and dispensed outside of the housing. The novel implantable device according to the present invention is designed as either a temporary or a permanent device to be implanted in a patient's body, particularly, at any location on or within the patient's body such as a particular site within tissue or organs.

Another embodiment of the present invention is a novel method for manufacturing an orifice mechanism. The novel method in accordance with the present invention comprises the steps of providing a mandrel, i.e. any member which serves as an inner member or core, wherein the mandrel has a certain length. A winding is then helically wound around at least a portion of the length of the mandrel.

The mandrel and the winding define a first channel for carrying a drug therethrough (an active channel). An inlet is at one end of the winding and an outlet is at another end of the winding for ingress and egress of the drug respectively.

Another embodiment in accordance with the present invention is directed to an orifice device for delivering one or more drugs. The orifice device comprises:

an inner member having a proximal end and a distal end;
a winding helically wound around the inner member, the winding comprising a plurality of distinct wires helically wound in parallel around the inner member;
the winding and the inner member defining at least three separate channels for carrying one or more drugs therethrough and an inlet at the proximal end of the winding and an outlet at the distal end of the winding for the plurality of distinct wires.

The orifice device according to the present invention has at least two of the plurality of distinct wires with a different dimension such as their outer circumference, diameter or cross-sectional area. Additionally, an outer member is used or placed over the winding. The outer member can be a sheath. In some embodiments according to the present invention, at least two of the at least three separate channels have a different fluid flow rate. And, in some embodiments, at least two of the at least three separate channels carry a different drug.

In some embodiments, the orifice device has an outer member that comprises channel filling material for blocking drug flow through one of the at least three separate channels. The channel filling material is a glue or an adhesive or the like.

Additionally, the wire used for the plurality of distinct wires can have any desired shape such as a circular shape in cross-section, a hexagonal shape in cross-section, an octagonal shape in cross-section, a triangular shape in cross-section, etc.

Moreover, the outer member or sheath is made of a polymer material such as PTFE. Additionally, the wire used for the plurality of distinct wires is made of a degradation-resistant material such as a nickel titanium alloy, stainless steel alloy or plastic. The wire has a width ranging from 0.001-0.050 inches. And, preferably, the wire has a width ranging from 0.004-0.005 inches.

Another embodiment in accordance with the present invention is directed to an orifice device for delivering one or more drugs. The orifice device comprises:

an inner member having a proximal end and a distal end;
a plurality of windings helically wound around the inner member, each winding defining a separate layer, each winding comprising at least one wire helically wound around the inner member;
the plurality of windings and the inner member defining at least two separate channels for carrying one or more drugs therethrough and an inlet at the proximal end of each of the plurality of windings and an outlet at the distal end of the plurality of winding.

At least one of the plurality of windings has a plurality of distinct wires helically wound in parallel around the inner member and at least one of the plurality of windings respectively. The plurality of windings and the inner member define at least three separate channels for carrying one or more drugs therethrough. Additionally, in some embodiments, at least two of the plurality of distinct wires have a different dimension such as their outer circumference, diameter or cross-sectional area, etc.

Moreover, the orifice device further comprises an outer member over the plurality of windings. The outer member can be a sheath. Moreover, the outer member or sheath is made of a polymer material which can be PTFE. Additionally, the wire used for the plurality of distinct wires is made of a degradation-resistant material such as a nickel titanium alloy, stainless steel alloy or plastic. The wire has a width ranging from 0.001-0.050 inches. And, preferably, the wire has a width ranging from 0.004-0.005 inches.

In some embodiments according to the present invention, at least one of the at least two separate channels has a different fluid flow rate. Additionally, in some embodiments according to the present invention, at least two of the at least three separate channels have a different fluid flow rate. Moreover, in some embodiments, at least one of the at least two separate channels carry a different drug. And, in other embodiments, at least two of the at least three separate channels carry a different drug.

In other embodiments, the orifice device according to the present invention comprises channel filling material for blocking drug flow through one of the at least two separate channels.

In other embodiments, the orifice device has an outer member that comprises channel filling material for blocking drug flow through one of the at least three separate channels. The channel filling material is a glue or an adhesive or the like.

Additionally, the wire used for the plurality of distinct wires can have any desired shape such as a circular shape in cross-section, a hexagonal shape in cross-section, an octagonal shape in cross-section, a triangular shape in cross-section, etc.

In some embodiments according to the present invention, the orifice device also includes an outer member between at least one of the plurality of windings, i.e. an intermediate member. This outer member can also be a sleeve and can be made of the same or a different material.

In some embodiments, the plurality of windings and the inner member define at least four separate channels for carrying one or more drugs therethrough. Additionally, at least one of the at least four separate channels has a different fluid flow rate. And, in some embodiments, at least one of the at least four separate channels carries a different drug therethrough. In other embodiments, each of the at least four separate channels has a different fluid flow rate. And, in some embodiments, each of the at least four separate channels carries a different drug therethrough.

All embodiments of the present invention are directed toward a simple orifice design that allows for exceptionally low fluid flow rates by creating an extremely long orifice with a very small cross-sectional area that is ideal for very compact spaces. The use of a helical winding for all embodiments of the present invention results in a simple helical wire wrap that creates a very long orifice and results in primary benefits such as simplicity, compactness, readily adaptable design and customizable designs, ease of manufacturing and low costs of parts for manufacturing. The flexibility and adaptability of the present invention is exhibited by the properties of the orifice in accordance with the present invention that can be easily modified, for instance, by selecting a winding (comprised of any desired wire type) using wires of different diameters and also by varying the length of the helix (helical winding). Assembly and manufacturing of the orifice in accordance with the present invention is extremely flexible and simple especially since no precision machining is required such as the precise machining or complex and expensive injection molding equipment associated with the prior art devices and their manufacturing methods.

DESCRIPTION OF THE PREFERRED EMBODIMENTS

The present invention is directed toward a novel orifice mechanism, generally designated 200, (interchangeably and commonly referred to herein as "orifice mechanism", "orifice feature", "orifice", "regulator", "regulator mechanism", "regulator device", or "orifice device") such as reflected in embodiments of the present invention shown in FIGS. 1A, 1B, 2A, 2B, FIG. 3, FIG. 4, FIG. 5, FIG. 6, FIG. 7, FIG. 10A, 10B, FIG. 11A, 11B, FIG. 12, and FIG. 13.

Figure 8:
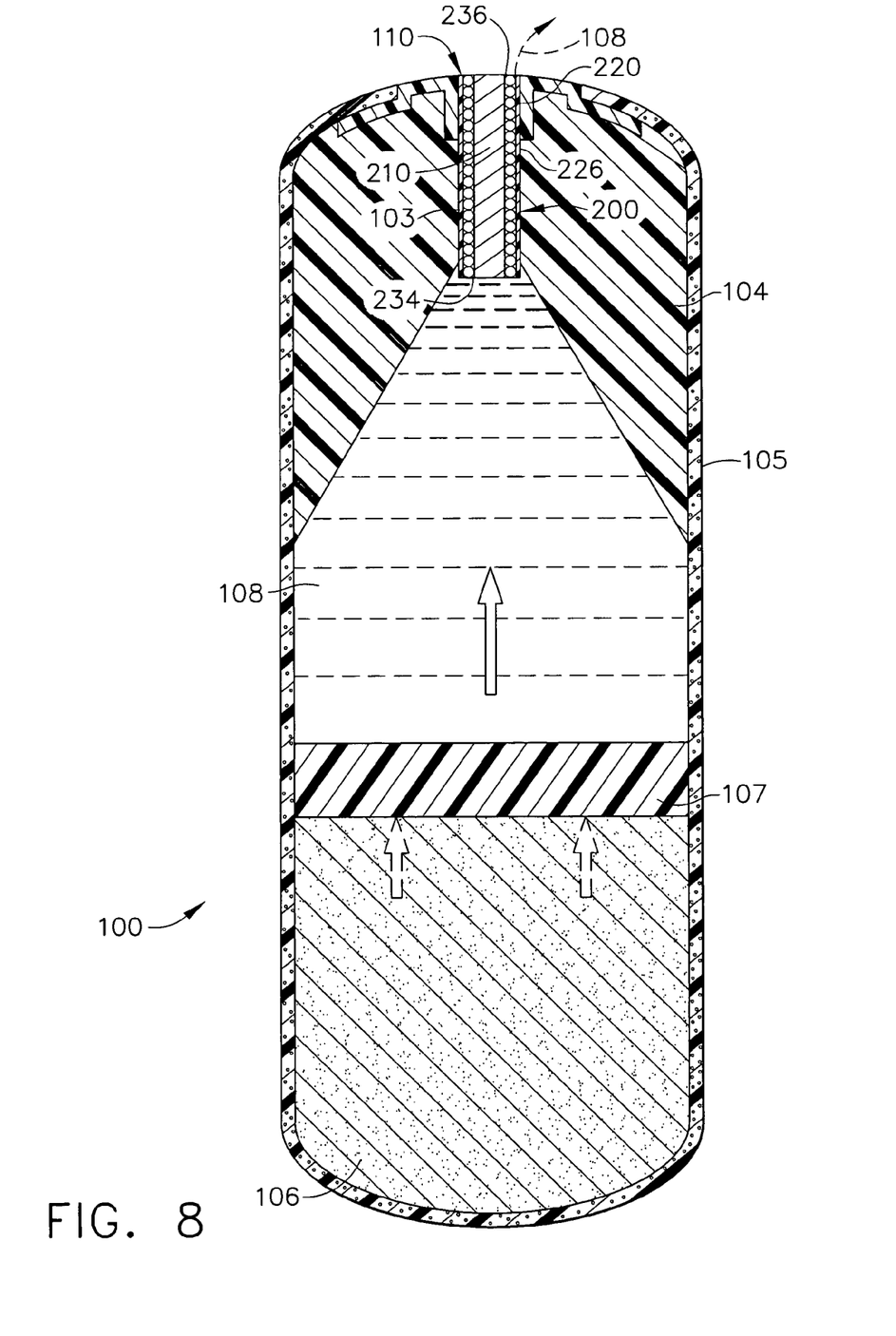
FIG. 8 is a view in cross-section of an implantable drug delivery device having an orifice mechanism in accordance with the present invention.

The present invention is also directed toward a novel drug delivery device such as an implantable device, generally designated 100, shown in FIG. 8 and includes any type of implantable device such as an implantable drug delivery device, implantable drug elusion device, implantable drug delivery pumps or the like. The novel drug delivery device 100 of this embodiment also includes the novel orifice mechanism 200.

Figure 9:
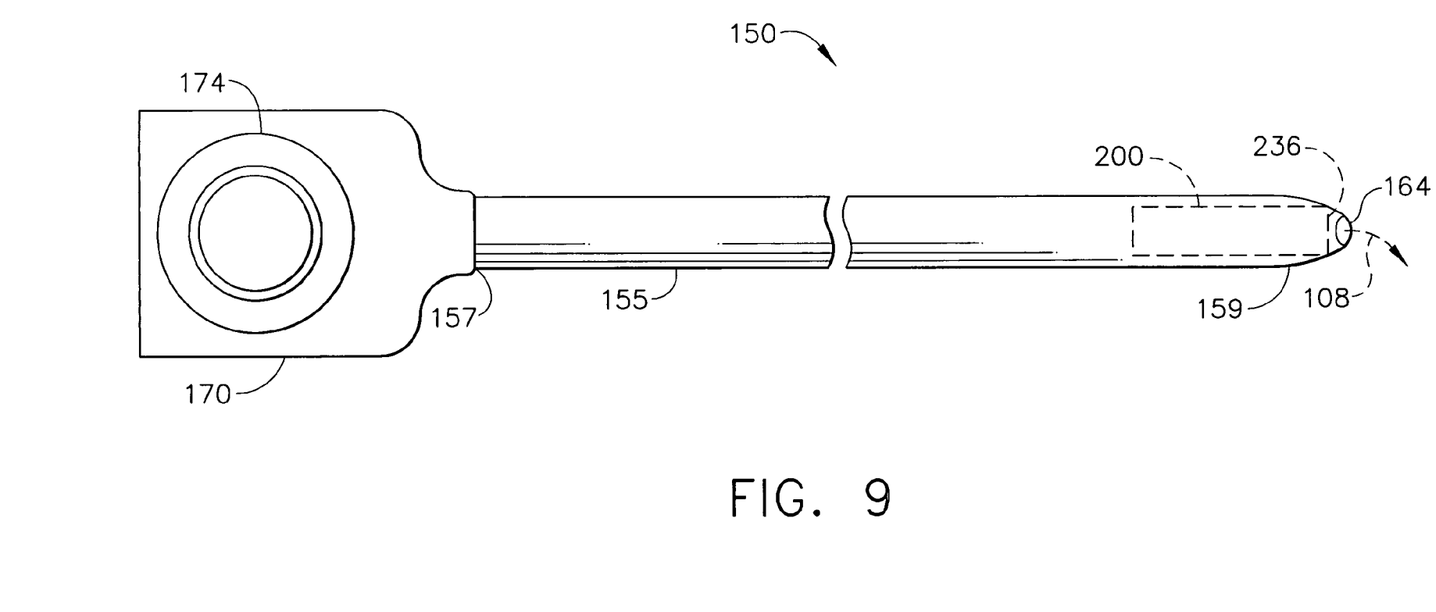
FIG. 9 is a side view of an elongated drug delivery device having an orifice mechanism in accordance with the present invention

The present invention is also directed toward a novel drug delivery device 150 having an elongated body 155 utilizing the orifice mechanism 200 in accordance with the present invention which is used at a desired location on the body 155 of the drug delivery device 150 such as shown in FIG. 9. The drug delivery device 150 in accordance with the present invention in this embodiment shown in FIG. 9 is directed toward drug delivery devices such as drug delivery catheters having elongated and/or flexible bodies and also include intravenous (IV) drug catheters such as IV drug catheters or IV drug delivery ports or local drug delivery catheters.

Figure 1A:
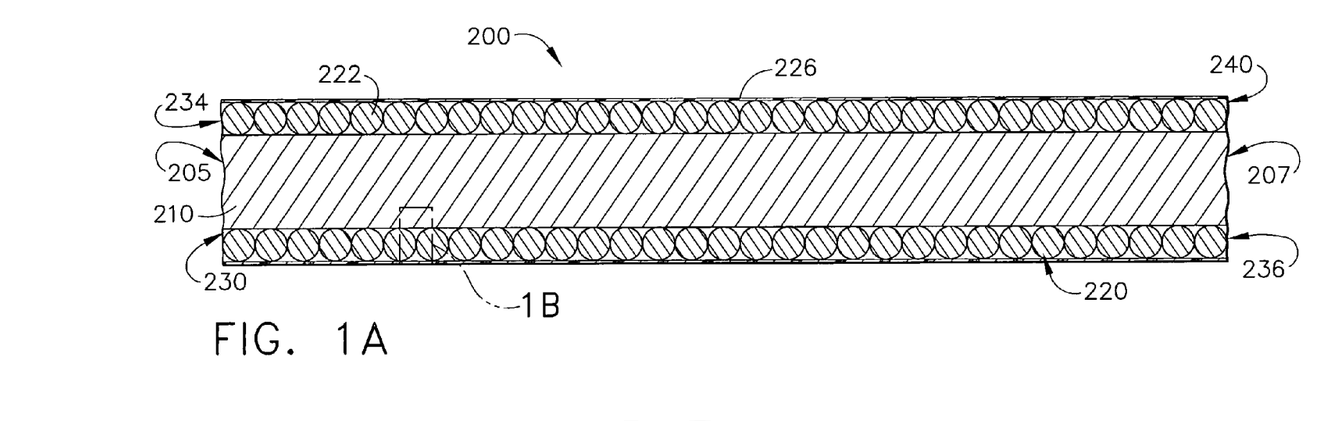
FIG. 1A is an elevated side view of an orifice device in cross-section having a two-channel design in accordance with the present invention.
Figure 2A:
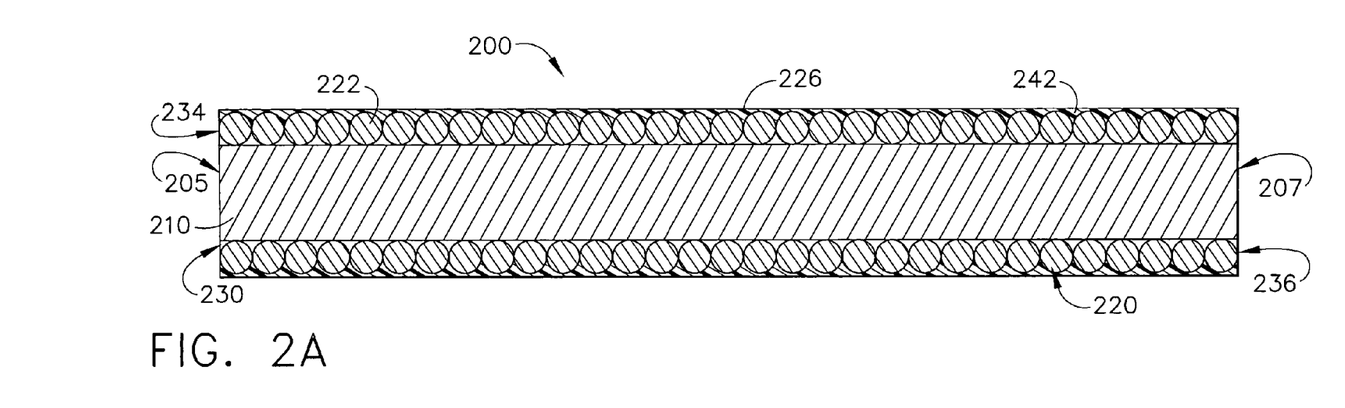
FIG. 2A is an elevated side view of an alternative embodiment of an orifice device in cross section having a one-channel design in accordance with the present invention.

The present invention is also directed toward a novel method of manufacturing the orifice mechanism 200 in accordance with the present invention and as best illustrated in FIG. 1A and FIG. 2A.

As best shown in FIGS. 1A, 1B, 2A and 2B, the novel orifice device or mechanism 200 in accordance with the present invention has a first end or proximal end 205 and a second end or distal end 207 respectively. The first component of the orifice mechanism 200 in accordance with the present invention is an inner member 210 which serves as an inner core for the device 200 and is used as a mandrel in the manufacturing method in accordance with the present invention. The inner member 210 has a length of any desired dimension and a winding 220 comprising a wire strand (wire) 222 helically wound or helically wrapped around the inner member (mandrel) 210 along any desired portion of the inner member 210. For example, the wire 222 of the winding 220 extends from the proximal end 205 to the distal end 207 of the orifice mechanism 200 as illustrated in FIGS. 1A and 2A, however, the winding 220 can be located along any portion of the length of the inner member 210 and comprises any desired width or dimension along the length of the inner member 210.

The wire 222 of the winding 220 is wound or wrapped around the inner member 210 in any desired or customized fashion in order to create any desired pitch (channel depth) and amplitude (distance between adjacent individual strands of wire 222) in order to customize a first drug delivery channel or inner drug delivery channel 230. This first drug delivery channel is also known as an active channel. The first drug delivery channel 230 is an interior channel formed by the individual strands of the wire 222 of the winding 220 and an outer member 226 which is an exterior surface placed over and around the winding 220 and inner member 210. The outer member 226 serves as an exterior surface which constrains the winding 220 (and individual strands of wire 222) and the inner member 210 such that the outer member 226, the wire 222 of the winding 220, and the inner member 210 (mandrel) define a second drug delivery channel or exterior channel formed by the remaining or unfilled interstices or interstitial spaces. The second drug delivery channel is also an active channel. The outer member 226 can be any type of member such as a sleeve or a tube as relevant examples, and can be made of any material such as a polymer material, for instance, PTFE, or even be made entirely of an adhesive material such as a glue.

Figure 1B:
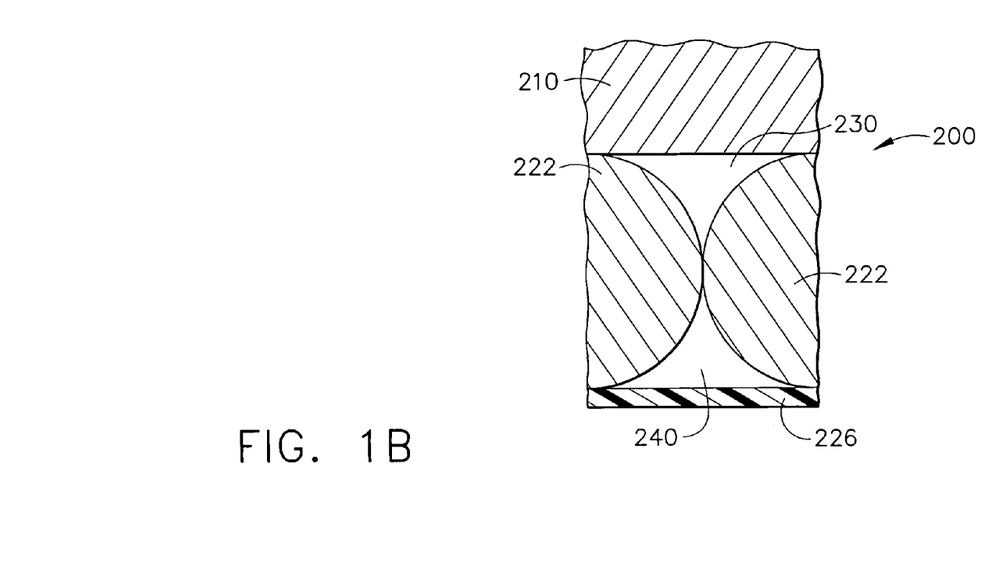
FIG. 1B is an enlarged view of a portion of the orifice device of FIG. 1A showing a coil as part of a winding and having a circular-shaped cross-section.
Figure 2B:
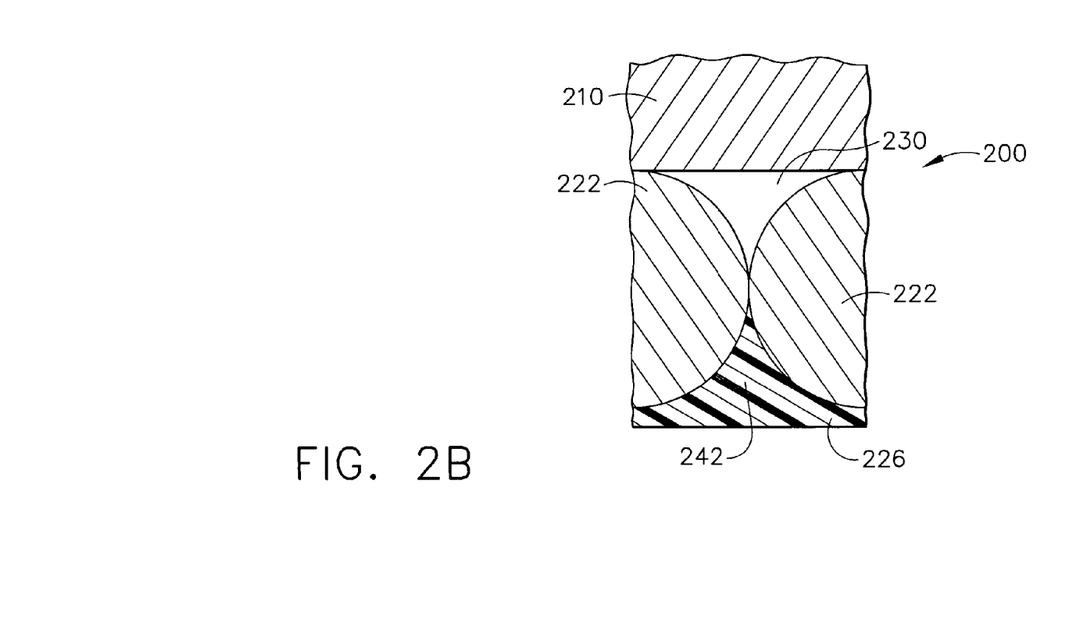
FIG. 2B is an enlarged view of a portion of the orifice device of FIG. 2A showing a coil as part of a winding and having a circular-shaped cross-section.
Figure 3:
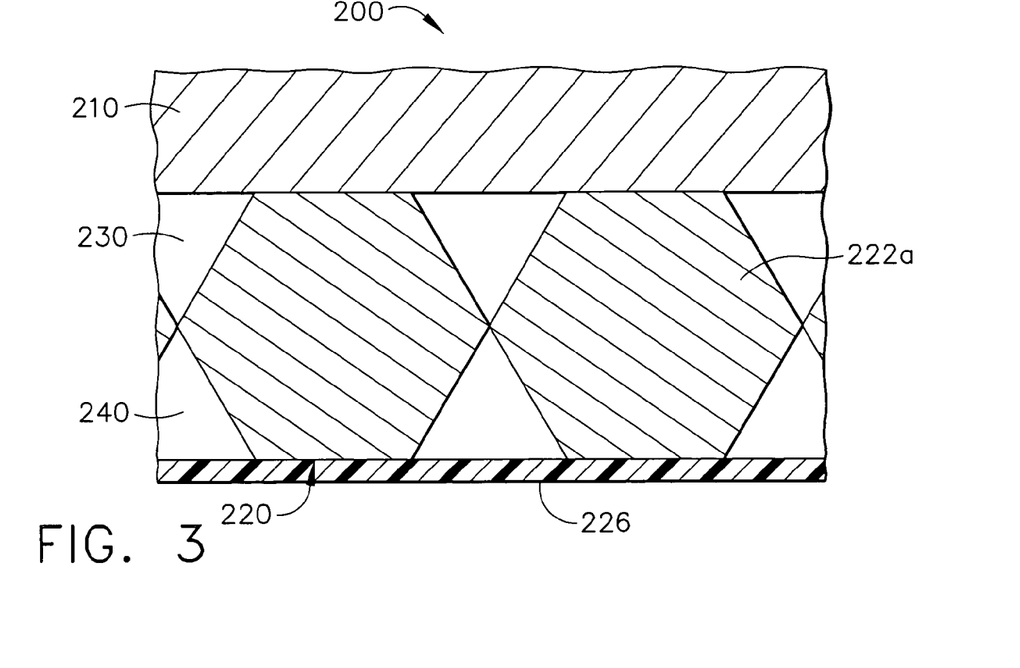
FIG. 3 is an enlarged view of a portion of the orifice device of FIG. 1A wherein the coil has a hexagonal shape in cross-section.
Figure 4:
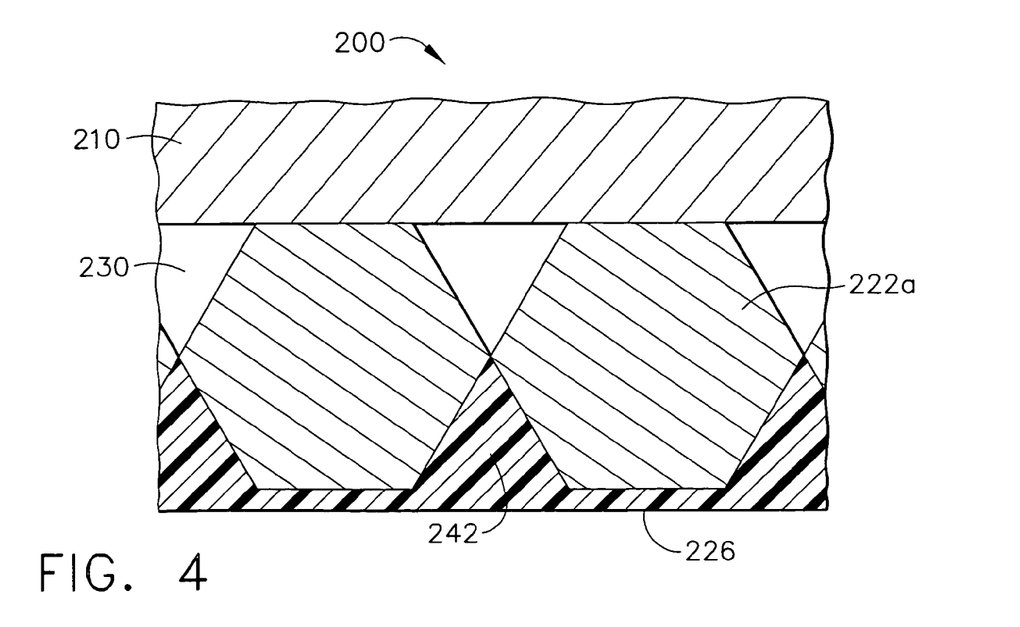
FIG. 4 is an enlarged view of a portion of the orifice device of FIG. 2A wherein the coil has a hexagonal shape in cross-section.
Figure 5:
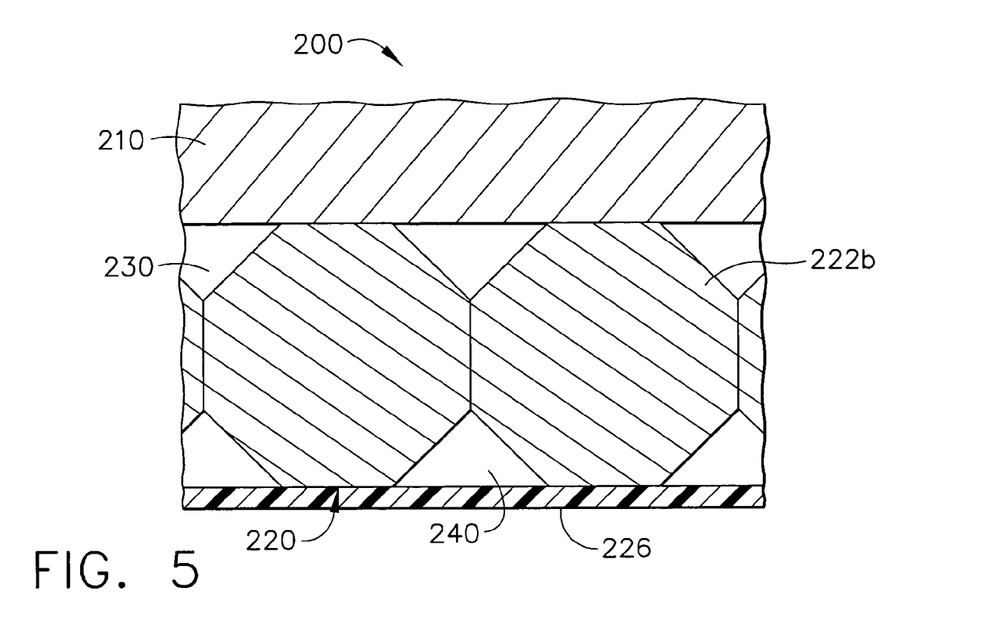
FIG. 5 is an enlarged view of a portion of the orifice device of FIG. 1A wherein the coil has an octagonal shape in cross-section.
Figure 6:
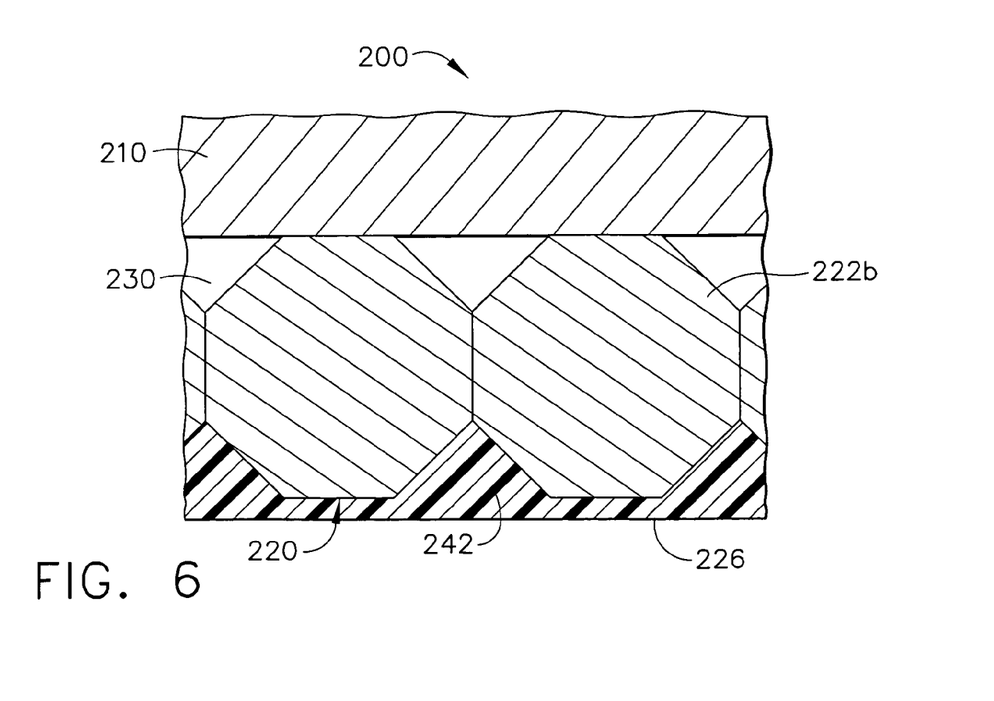
FIG. 6 is an enlarged view of a potion of the orifice device of FIG. 2A wherein the coil has an octagonal shape in cross-section.
Figure 7:
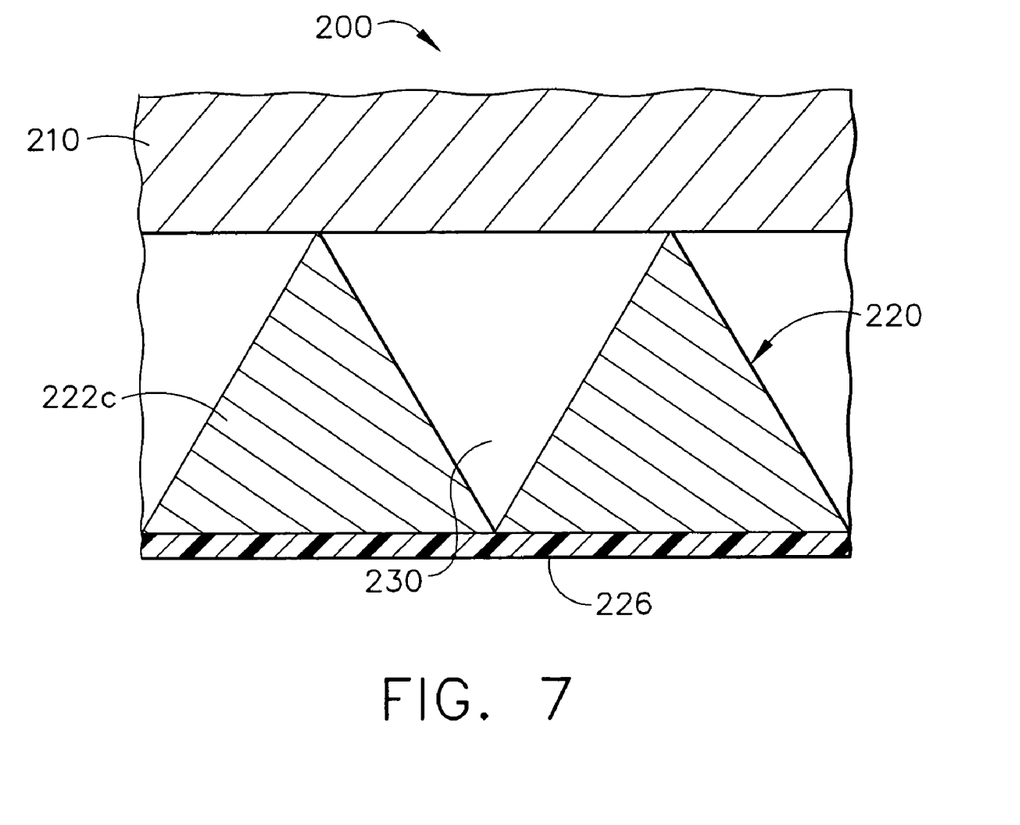
FIG. 7 is an enlarged view of a portion of the orifice device of FIG. 2A wherein the coil has a triangular shape in cross-section.

The wire 222 is made of a degradation resistant material in order to resist erosion or degradation by the constituents or properties of the drug or by exerted forces applied by the drug 108 (FIG. 8) when delivered or channeled through the interior channel 230 (FIGS. 1A, 1B, 2A and 2B) and the exterior channel 240 (FIGS. 1A and 1B). Examples of degradation resistant materials for use with the wire 222 in accordance with the present invention include materials such as a nickel titanium alloy, i.e. Nitinol (NiTi), stainless steel alloys, plastic or other types of relevant polymers. As best illustrated in FIGS. 1B, 2B, 3, 4, 5, 6 and 7, the wire 222 comprises any desired cross-sectional shape or configuration. Although not limited to these particular depicted cross-sectional shapes or configurations, relevant examples of the wire 222 in accordance with the present invention include wire 222 having a circular-shaped cross-sectional configuration as shown in FIG. 1B and FIG. 2B; wire 222a having a hexagonal shape in cross-section as shown in FIG. 3 and FIG. 4; octagonal-shape wire 222b as shown in FIG. 5 and FIG. 6; and triangular-shape wire 222c in cross-section as shown in FIG. 7.

When manufacturing the orifice mechanism 200 in accordance with the present invention, the interior channel (the inside or interior set of interstices) 230 or exterior channel (the exterior or outside set of interstices) 240 can be blocked in order to created a one-channel or one-side design or approach in order to further reduce the flow of the drug 108 (FIG. 8) or to ease the burden of manufacturing. For example, this can be accomplished without precise sizing of the outer member 226, and instead can be accomplished through the use of a polymer material or glue as the outer member 226 in lieu of an outer member 226 as a sleeve or tube. Thus, in a one-channel design, channel filling material 242 (FIG. 2B, FIG. 4, and FIG. 6) is used to occlude or block one of either the interior channel (interior interstices) 230 or exterior channel (exterior interstices) 240 as shown. For example, in the embodiments shown, it is the exterior channel (exterior interstices) 240 that is replaced by the channel filling material 242, i.e. the polymer material or glue. Although not shown, alternatively, the channel filling material 242 is used to occlude, block or fill the interior channel (interior interstices) 230 as part of a one-channel design. Additionally, the channel filling material 242 can be either the same material as used with the outer member 226 or be made of a second different material.

Accordingly, in accordance with the manufacturing method of the present invention, the orifice device or orifice mechanism 200 is adaptable to a tailored or customizable manufacturing method determined by control factors in accordance with the present invention. Thus, the present invention allows for customizing these central factors upon demand and include overall length of the winding 220, cross-sectional area of the wire 222 (to include the alternative wire embodiments 222a, 222b and 222c), shapes or configurations of all wire configurations, and dimensions of the interstices or channels, i.e. interior channel 230 and/or exterior channel 240; and the amount of constrain or fit of outer member 226 to include the dimensions, shape and specific material of the outer member 226. Thus, all of these factors controlled by the manufacturing method in accordance with the present invention allows for a customized orifice or orifice mechanism 200 that allows for varying rates of fluid flow control or regulation for the drug 108 (FIG. 8).

As a drug delivery feature, the orifice device or orifice mechanism 200 includes an inlet 234 located at the first strand of wire 222 at the inner member 210, for example, located at the proximal end 205 of the orifice mechanism 200. The inlet 234 is the starting point or entry point for ingress of the drug 108 (FIG. 8) into the first channel or interior channel 230 for carrying and channeling therethrough and terminates in an outlet 236 at the last strand of wire 222 of the winding 220 at the opposite end of the winding 220, for example, at the distal end 207 of the orifice mechanism 200. The outlet 236 allows for the channeled drug 108 (FIG. 8) to exit or egress from the last strand of wire 222 of the winding 220, for example, at distal end 207. As shown in FIG. 1A, the inlet 234 and the outlet 236 will exist at the interior channel or first channel 230 and the second channel or exterior channel 240 respectively as shown such that both channels 230 and 240 are active channels. As shown in FIG. 2A, the inlet 234 and the outlet 236 will exist for the first channel or interior channel 230 only. Thus, the channel filling material 242 of the outer member 226 prevents ingress, channeling and egress of any drug 108 through any other portion of the orifice device 200 except for the first channel or inner channel 230, for example, channeling is only possible through the interior interstices defined by the interior channel 230. Accordingly, in this example, inner channel 230 is the only active channel capable of channeling the drug 108 through its interstices.

Relevant examples of degradation resistant material for the winding 220, i.e. wire 222 (FIG. 1A, FIG. 1B, FIG. 2A and FIG. 2B), wire 222a (FIG. 3 and FIG. 4), 222b (FIG. 5 and FIG. 6), and 222c (FIG. 7), also include various types of metal such as stainless steel alloys, nickel titanium alloys (Nitinol, NiTi), MP35N, and Titanium as well as various types of polymers or plastics.

Moreover, any size or dimensions for the winding 220 and wire 222, 222a, 222b and 222c respectively can be utilized. For instance, one example of appropriate dimensions for the wire is to use wire having a strand with a width ranging from 0.001-0.050 inches. Additionally, another preferable example for the wire dimensions in accordance with the present invention, is to utilize a wire having strands with a width ranging from 0.004-0.005 inches.

The present invention also is directed toward an implantable drug delivery device, generally designated 100, which includes implantable devices such as a drug delivery pump. In one example according to the present invention, the drug delivery device 100 is an implantable drug pump which utilizes the orifice mechanism 200 and a source of drug 108.

FIG. 8, shows orifice mechanism 200 in an implantable pump device 100 such as an osmotically driven ruminal bolus. The orifice 200 resides in space 103 which passes through a densifier 104. The bolus is surrounded by a semipermeable membrane 105. The semipermeable membrane 105 allows water to pass therethrough which is imbibed by swellable osmotic element 106 which abuts or contacts movable interface 107 and upon imbibing, the water exerts force upon moveable interface 107 which in turn forces the drug 108 out of the orifice 200 through the outlet 236.

The semipermeable mebrane 105 serves as a housing. Additionally, the membrane or housing 105 has an opening 110 therein and in fluid communication with the outlet 236 of the orifice mechanism 200. This permits the drug 108 to be carried by and channeled out of the orifice mechanism 200 and the membrane or housing 105 respectively in order to provide systemic or localized drug delivery.

The present invention is also intended to be not only an implantable drug device, but also intended to be used as a temporary implant device, for example a device wherein all of the components of the device 100, including the orifice mechanism 200, are made of a biocompatible and biodegradable material. Additionally, the drug delivery device 100 is also intended to be used as a device for placement within a body cavity, for example, the nasal cavity, ear canal, mouth, sinus passageway, the eye to include any vitreous passageway, the rectum or the like. Furthermore, the drug delivery device 100 is also intended to be used at an exterior surface of the patient, for example, placed at a location somewhere on the patient's skin for local delivery of the drug 108 to an exterior treatment site on the skins surface or for absorption into the patient's bloodstream through the skin or directly into a wound.

In the drug delivery device embodiment illustrated in FIG. 8, the densifier 104, housing/membrane 105, swellable osmotic element 106 and moveable interface 107 (which can be a piston) operate as a driving system or pumping system for the drug 108 by working in combination to move the drug 108 into inlet 234, through the appropriate interstices or channels (for instance, first channel and/or second channel), and out of the outlet 236 and housing 105 through the opening 110 in housing 105.

FIG. 9 illustrates another embodiment of a drug delivery device, generally designated 150, such as an intravascular device. Relevant examples of the device 150 include a catheter, intravenous (IV) port device or the like. In some instances in accordance with the present invention, the drug delivery device 150 includes a body 155, such as an elongated body, having a proximal end 157 and a distal end 159 respectively and a lumen therein in fluid communication with the proximal end 157 and the distal end 159. A distal end opening 164 is located at the distal end 159 of the body 155. And, the orifice mechanism 200 is located on the body 155, for example within the lumen of body 155 and at the distal end 159 and adjacent to and in fluid communication with the opening 164. The body 155 serves as the outer member 226 (FIGS. 1A-8) and provides similar function and is comprised of similar materials as used with the outer member 226 (detailed above). The outlet 236 of the orifice mechanism 200 is located near the opening 164 and is in fluid communication therewith such that the drug 108 is passed through the orifice mechanism 200 (as described above) and out of the outlet 236 and opening 164 respectively.

Additionally, the delivery device 150 includes a handle 170 located at the proximal end 157 of the body 155. The handle also includes a control 174 for controlling movement of the distal end 159 of the device 150. Relevant movement of the distal end 159 includes deflection of the distal end 159 and opening 164 in various directions, for example, in any desired direction or angle offset from the longitudinal access of the body 155. Although not shown, the device 150 can either include the source of drug 108 at a location within the lumen body of 155 or can receive the source of drug 108 at any desired portion of the device 150, for example, through an entry port in the handle 170 (not shown). Accordingly, an entry or access port in the handle 170 can be shaped to accommodate a standard needle syringe containing the source of drug 108 such that the drug 108 can be injected or infused into the body 155 of the device 150 through the entry or access port for feeding or supplying drug 108 to the orifice mechanism 200 for ultimate delivery through the opening 164 of the device 150. In addition to the design and control factors mentioned above that are responsible for the fluid flow rate of the drug 108, the drug 108 is also channeled or migrates through the orifice mechanism 200 through capillary action which is controlled by many of the parameters and features outlined above to include tightness of the winding 220 (helical coil), diameter or width of the strands of wire (222, 222a, 222b and 222c respectively) and viscosity of the drug 108 being delivered. All of these parameters can be adjusted in order to optimize the fluid flow rate for the drug 108. Additionally, additives can be included with the drug 108 (in solution) in order to control the viscosity of the drug 108 thereby controlling the overall delivery fluid flow rate.

Moreover, as mentioned above, one benefit of the orifice mechanism or orifice device 200 in accordance with the present invention is the ability to achieve very low fluid flow rates through the use of a tight, economic and cost efficient manufactured winding 220. Thus, the present invention allows for more efficient manufacturing, less parts and less manufacturing tooling normally associated with the traditional and more costly parts, tools and manufacturing methods associated with the prior art drug delivery devices. Accordingly, the present invention avoids these drawbacks associated with the prior art devices such as costly machining normally found with lathe machines, micro-drilling or even injection molding machines that are required for manufacturing these prior art devices.

Alternative embodiments for the orifice mechanism 200 in accordance with the present invention, are best depicted in FIGS. 10A and 10B, 11A and 11B, FIG. 12 and FIG. 13. The orifice mechanism 200a (FIGS. 10A and 10B), 200b (FIGS. 11A and 11B), 200c (FIG. 12) and 200d (FIG. 13) in accordance with these alternative embodiments of the present invention have the same or substantially similar features, elements and their functions as detailed above for the orifice mechanism embodiments of FIGS. 1-9 above. Likewise, the same reference numerals are used to designate like or similar features and their function for these orifice mechanism embodiments of FIGS. 10A, 10B, 11A, 11B, 12 and 13 in accordance with the present invention.

As described above for the orifice mechanism 200 depicted in FIGS. 1-7, the alternative embodiments for orifice mechanism 200a, 200b, 200c and 200d in accordance with the present invention are also capable of being used in the implantable drug delivery device depicted in FIG. 8 and the elongated drug delivery device depicted in FIG. 9 as both described previously above.

Figure 11A:
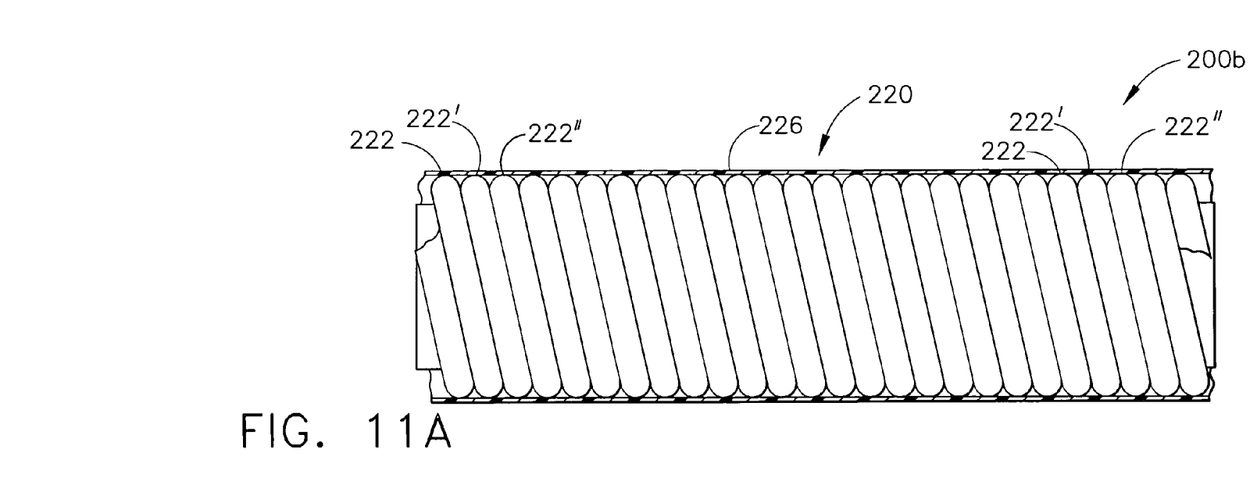
FIG. 11A is partial perspective view of an alternative embodiment of an orifice device having a winding comprising multiple, distinct wires in parallel in accordance with the present invention.
Figure 11B:
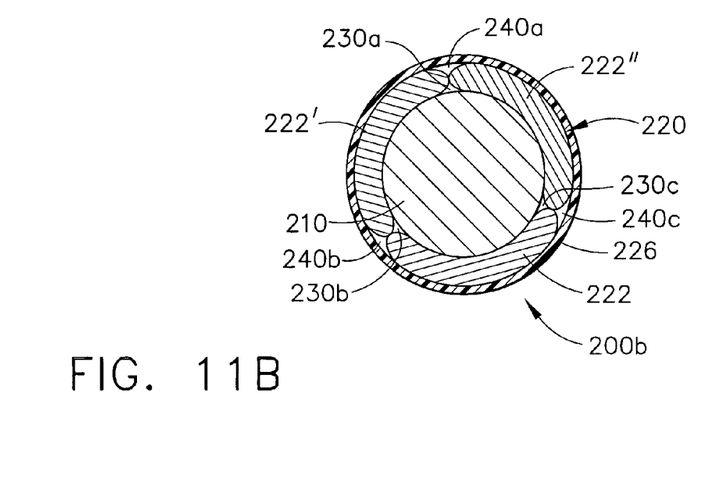
FIG. 11B is a view in cross-section of the device of FIG. 11.

A further alternative embodiment for the orifice mechanism is best illustrated in FIGS. 11A and 11B as orifice mechanism 200b having a plurality of distinct wires 222, 222' and 222" wrapped in parallel around the inner member of mandrel 210. This embodiment for an orifice mechanism 200b in accordance with the present invention comprises multiple wires 222, 222' and 222" helically wound in parallel around inner member 210 such that each of these multiple wires lies adjacent to a different or distinct wire respectively. Accordingly, as shown in FIG. 11B, coil or winding 220 comprises three distinct wires helically wrapped adjacent each other in tight formation thereby defining and resulting in a plurality of different fluid flow or drug delivery channels. For example, orifice mechanism 200b in this example depicts three separate wires 222, 222' and 222" respectively which when wrapped in parallel adjacent each other around inner member 210 define three distinct fluid flow or drug delivery channels (as inner channels) 230a, 230b and 230c respectively. Additionally, with the addition of outer member 226 which serves as an outer sleeve placed over an exterior portion or surface of wires 222, 222' and 222" respectively, three additional fluid flow or drug delivery channels 240a, 240b and 240c (as outer fluid flow or drug delivery channels) are also defined. Accordingly, a multiple wire orifice mechanism 200b having three separate wires 222, 222' and 222" have the ability to provide for up to six separate fluid flow or drug delivery channels as shown, i.e. three inner channels 230a, 230b and 230c and three outer channels 240a, 240b, and 240c.

Accordingly, inner channels 230a, 230b and 230c and outer channels 240a, 240b and 240c are all helical channels helically arranged around the longitudinal axis of inner member 210 or orifice mechanism 200b wherein each channel terminates at a distal end with its own separate outlet.

Additionally, each of these fluid flow channels 230a, 230b, 230c and 240a, 240b, and 240c can each have different or varying rates of fluid flow as well as the ability to each accommodate a different type of drug or fluid for delivery through each respective channel. Thus, the end-user has the ability to customize a drug delivery regimen or plan according to any desired pattern using any of the six different channels defined by the multiple wires.

Figure 12:
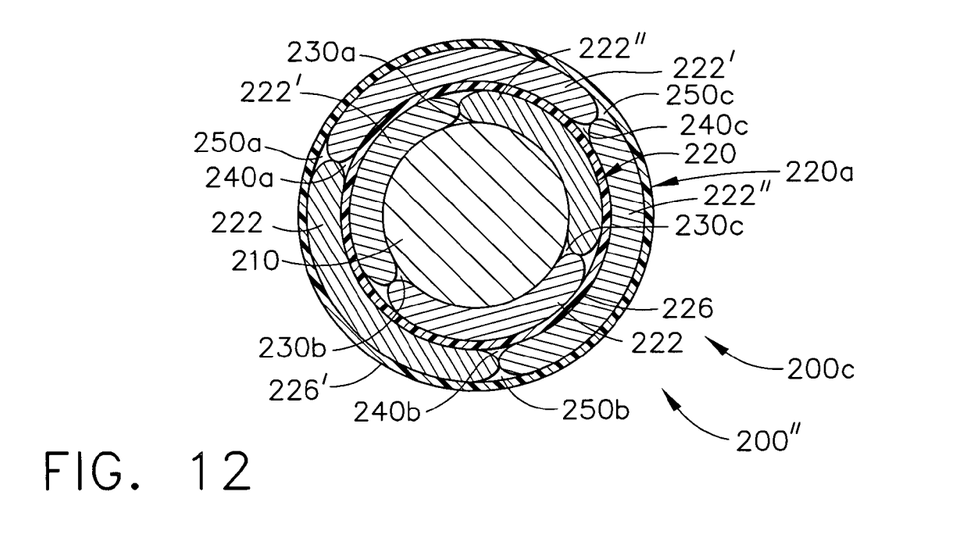
FIG. 12 is a view in cross-section of an alternative embodiment of an orifice device having a plurality of windings in a multiple layer, multiple channel design having multiple, distinct wires in parallel in accordance with the present invention.
Figure 13:
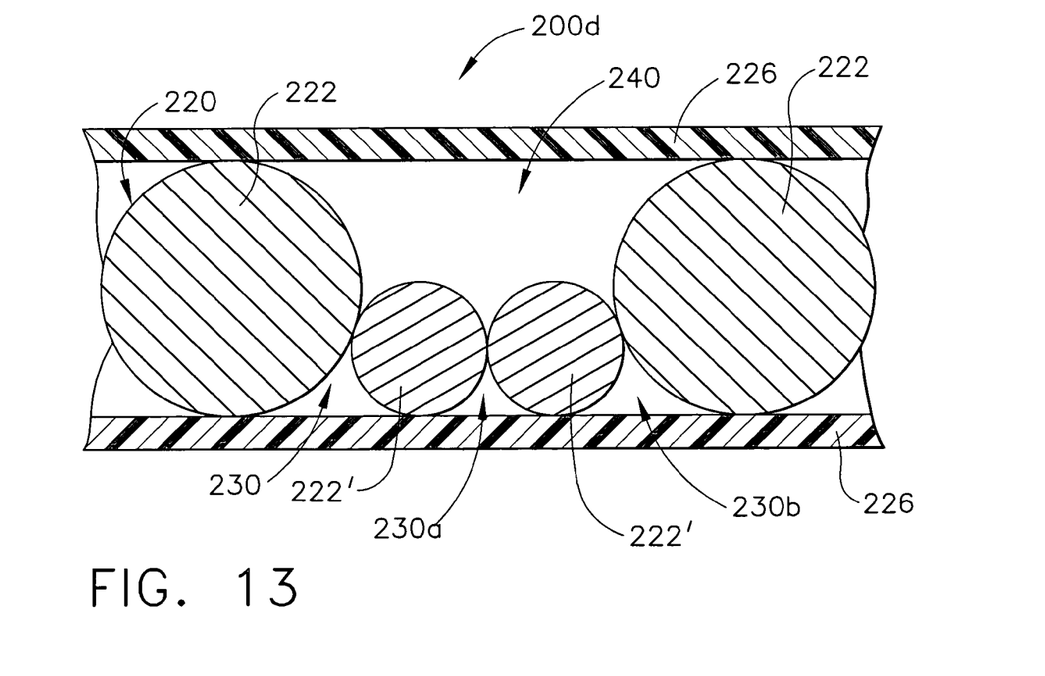
FIG. 13 is a partial view in cross-section of an alternative embodiment of an orifice device having a winding comprising multiple, distinct wires in parallel wherein at least some of wires have different dimensions and result in a multiple channel design such as a four-channel design in accordance with the present invention.

Furthermore, the three-wire example depicted in FIGS. 11A and 11B is for illustrative purposes only and it is important to note that any number of separate wires can be used to define a number of helical channels that are either less than or greater than the number of helical channels depicted in FIGS. 11A and 11B as well as the other multiple wire embodiments depicted in FIGS. 12 and 13.

Figure 10A:
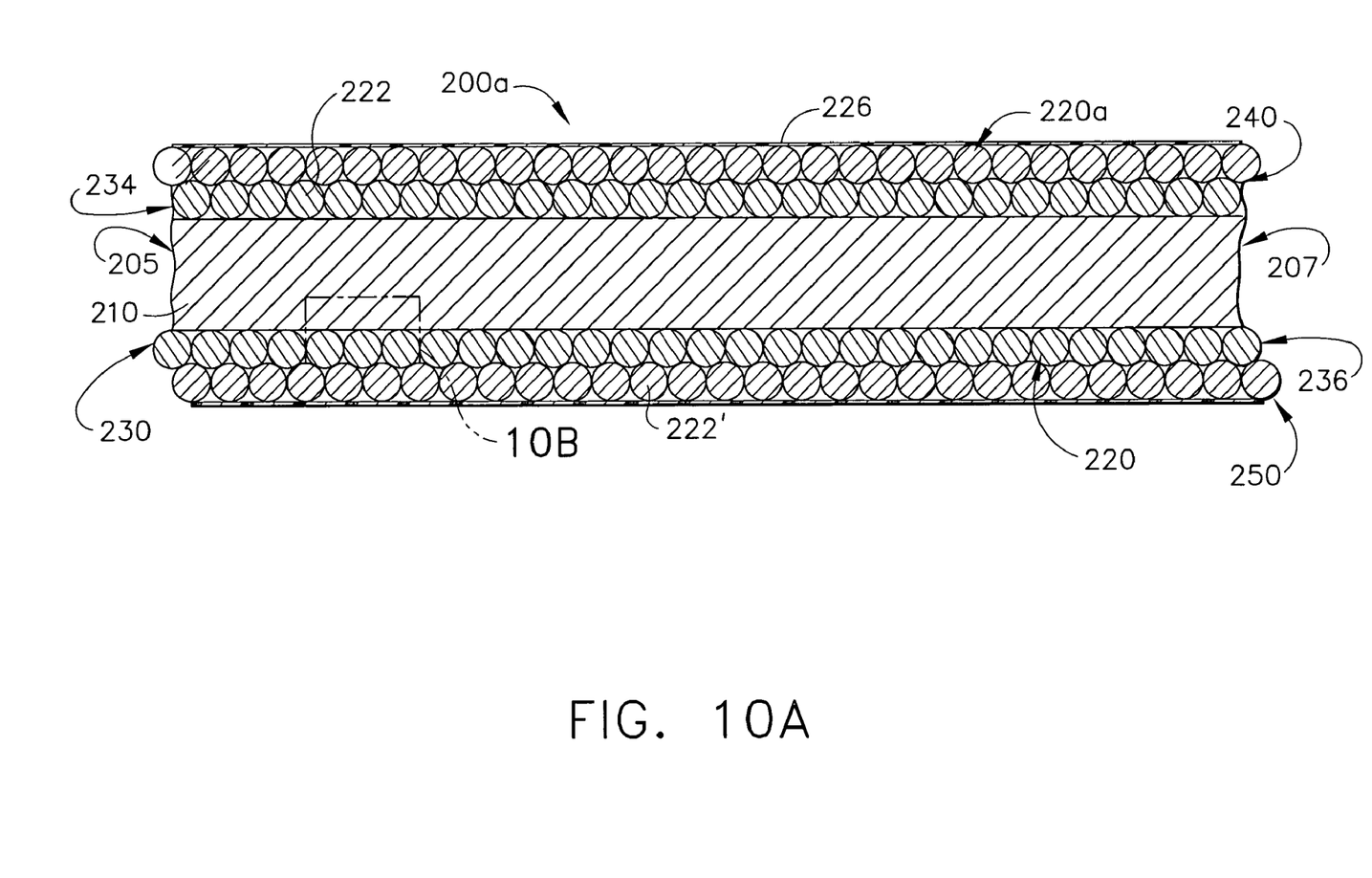
FIG. 10A is an elevated side view of an alternative embodiment of an orifice device in cross-section having a plurality of windings in a multiple layer, three-channel design in accordance with the present invention.
Figure 10B:
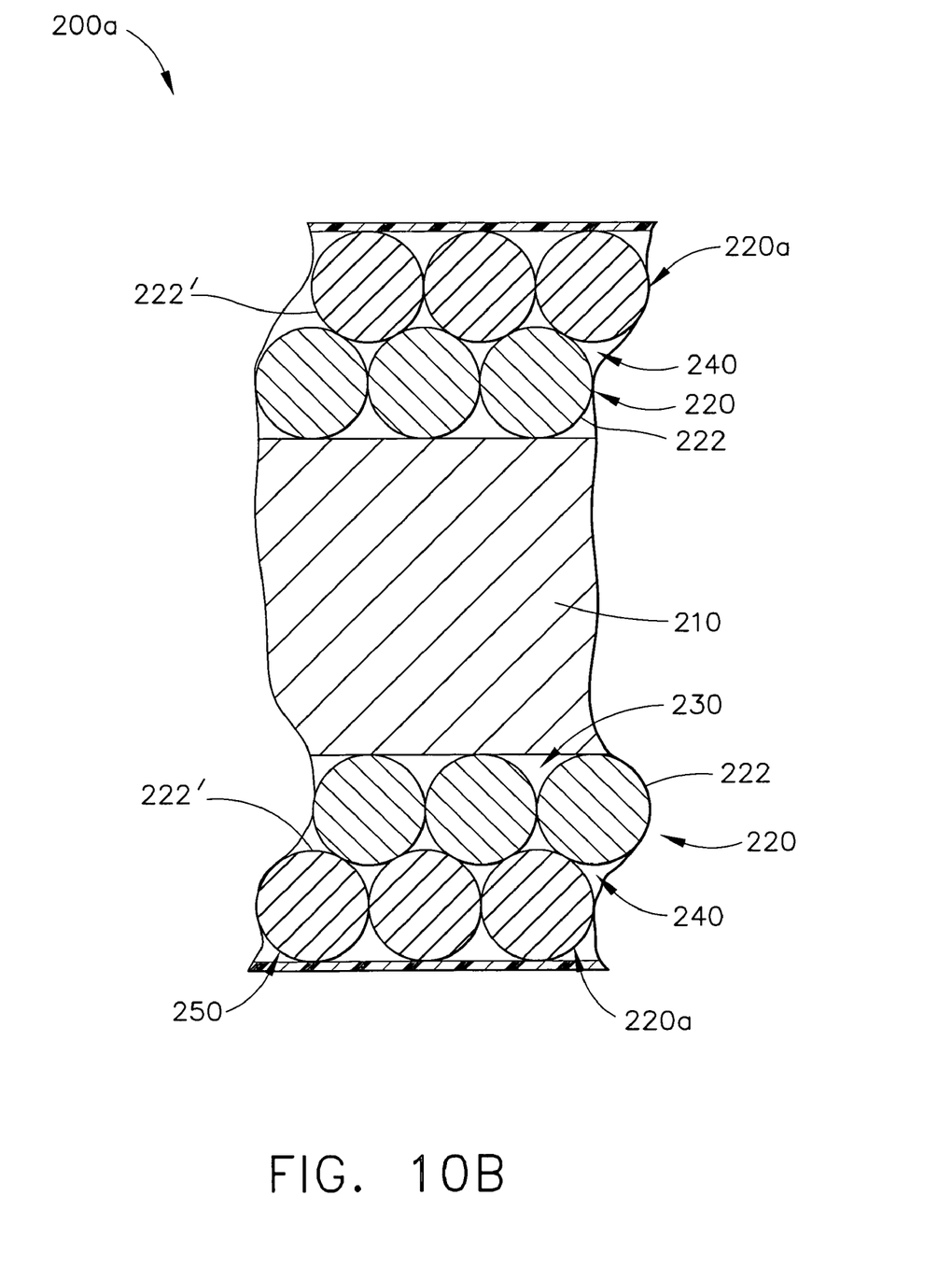
FIG. 10B is an enlarged view of a portion of the orifice device of FIG. 1A showing a coil wire as part of the winding for each layer wherein each wire has a circular-shaped cross-section.

FIG. 10A and FIG. 10B depict another embodiment for an orifice mechanism 200a in accordance with the present invention which is a multiple layer embodiment having a first or inner coil or winding 220 with wire 222' helically wound around inner member 210 (addressed previously in this disclosure) and a second or outer coil or winding 220a helically wound over an exterior surface or portion of the wire 222 of inner coil 220. Accordingly, wire 222' of outer coil 220a is wound into the spacing defining helical fluid flow channel or helical drug delivery channel 240. Thus, in this example, the multiple-layer orifice mechanism 200a provides for three separate helical drug delivery channels helically arranged around longitudinal axis of inner member 210, i.e. a first drug delivery channel or inner drug delivery channel 230, a second drug delivery channel or intermediate drug delivery channel 240, and a third drug delivery channel or outer drug delivery channel 250 as shown.

The third helical drug delivery channel or outer helical drug delivery channel 250 is created by the placement of outer member or outer sheath 226 over the exterior surface of the wire 222' of the outer coil 220a thereby creating the outer drug delivery channel 250.

Additionally, although not shown, another outer member or sleeve 226 can be placed between the inner coil 220 and the outer coil 220a (in order to serve as an intermediate member or intermediate sleeve) in order to create an orifice mechanism 200a having four separate and distinct drug delivery channels in multiple, parallel layers, i.e. a first channel created between wire 222 of inner coil 220 and inner member 210; a second channel created between wire 222 of the inner coil 220 and sleeve 226 (intermediate sleeve) interposed between inner coil 220 and outer coil 220a (not shown); a third channel created by the wire 222' of outer coil 220a and the intermediate sleeve 226 between inner coil 220 and outer coil 220a (not shown); and fourth channel created by wire 222' of outer coil 220a and outer sleeve 226 that is circumferentially wrapped around and covers outer coil 220a, inner coil 220 and inner member 210 respectively as shown.

Although FIG. 10A and FIG. 10B illustrate orifice mechanism 200a as a multi-layer orifice mechanism in accordance with the present invention having two distinct and stacked, parallel layers for drug delivery (resulting in multiple channel drug delivery such as four different helical channels), any number of multiple, stacked parallel layers can be used if desired. Accordingly, the multiple layer drug delivery orifice mechanism 200a in accordance with the present invention is not limited to only two separate stacked parallel layers, but can encompass any number of multiple stacked parallel layers desired.

Additionally, as best illustrated in FIG. 12, another alternative embodiment of another multiple-layer orifice mechanism 200c in accordance with the present invention also includes multiple wires 222, 222' and 222" helically wound or wrapped in parallel around inner member 210 (helically arranged around the longitudinal axis of inner member $210)_{13}$ for each coil 220, 220a, etc. in each respective multiple layer as shown. Accordingly, orifice mechanism 200c has the advantages of numerous multiple channels and multiple drug delivery layers for reasons such as delivering different drugs, varying fluid flow rates, customizing drug delivery regimens, etc. such as associated with the multiple wire embodiments and multiple layer embodiments addressed throughout this disclosure and described below.

As shown in FIG. 12, orifice mechanism 200c uses three distinct and separate wires 222, 222' and 222" for each of its two layers 220 and 220a respectively as just one illustrative example. Accordingly, by this example, the use of three separate wires 222, 222' and 222" results in as many as nine different helical channels. For instance, the first drug delivery channels or inner drug delivery channels 230a, 230b and 230c respectively resulting from wires 222, 222' and 222" helically wound around inner member 210 at first coil layer 220 as well as three intermediate channels 240a, 240b and 240c defined by the spacing between first coil layer 220 and second coil layer 220a as well as three additional outer channels 250a, 250b and 250c defined by the spacing between wires 222, 222' and 222" and outer sleeve 226' as shown. Sleeve 226 (which is optional in this embodiment) is used as an intermediate sleeve between first coil layer 220 and second coil layer 220a. Accordingly, when sleeve 226 is used as an intermediate sleeve along with outer sleeve 226' thereby containing first coil layer 220 and second coil layer 220a respectively, orifice mechanism 200c has twelve separate drug delivery channels in which any one or more of these twelve separate channels can be utilized as desired.

FIG. 13 illustrates an alternative embodiment for an orifice mechanism 200d having multiple wires wrapped in parallel such as described for orifice mechanism 200b (FIG. 11A and FIG. 11B described above) except that each of the separate wires 222 and 222' respectively have different dimensions or characteristics as shown. For example, as best illustrated in FIG. 13, the cross-sectional diameter for wire 222 is significantly greater than the cross-sectional diameter for adjacent parallel wire 222'. Additionally, the wire 222 and 222' can be arranged in any desired parallel arrangement such as the order or arrangement depicted in FIG. 13 resulting in adjacent wire strands that are the same, i.e. two adjacent strands of wire 222' in which each wire strand 222' is flanked on only one side by wire 222. It is important to note that any desired arrangement for the different parallel wires is contemplated by the present invention.

As shown in FIG. 13, orifice mechanism 200d define four different helical channels 230, 230a, 230b and 240 respectively wherein each channel has different or varying characteristics such as volume channeling space or volume channeling area as shown.

Again, similar to the channel function described above, the different channels 230, 230a, 230b and 240 can be used to provide one or more drugs at different fluid flow rates or one or more drugs throughout the different channels respectively. Accordingly, the four channels 230, 230a, 230b and 240 have the ability to channel or deliver four separate or different drugs.

Moreover, orifice mechanism 200d (although not shown) can also be a multiple-layer arrangement such as depicted in FIGS. 10A and 10B and FIG. 12 wherein each coil layer 220, 220a, etc. comprises multiple, separate wires 222, 222', etc.

that are distinct from each other such as having different dimensions, characteristics or the like for instance as shown in FIG. 13.

Orifice mechanisms 200*a*, 200*b*, 200*c* and 200*d* respectively provide for significant advantages of ensuring redundancy in drug delivery regimens or drug delivery plans such that drug delivery procedures can be continued in the event one or more channels are clogged or blocked or become inoperable for any reason. Additionally, orifice mechanisms 200*a*, 200*b*, 200*c* and 200*d* in accordance with the present invention provide the significant advantage of the ability to provide multiple drugs, i.e. one or more different drugs or different fluids or different fluid flow rates through the respective different channels or respective different layers such as shown and described above.

It will be appreciated that the preferred embodiments described above are cited by way of example and the full scope of the invention is limited only by the claims which follow.

What is claimed is:

1. An orifice device for delivering one or more drugs comprising:
   an inner member having a proximal end and a distal end;
   a plurality of windings helically wound around the inner member, each winding defining a separate layer, each winding comprising at least one wire helically wound around the inner member;
   the plurality of windings and the inner member defining at least two separate channels for carrying one or more drugs therethrough and an inlet at the proximal end of each of the plurality of windings and an outlet at the distal end of the plurality of windings, and an outer member over the plurality of windings, and an intermediate sleeve defining at least two channels between at least two of the plurality of windings, the intermediate sleeve being tubular with a smooth interior surface and smooth exterior surface from a proximal end of the intermediate sleeve to a distal end of the intermediate sleeve.

2. The orifice device according to claim 1, wherein at least one of the plurality of windings has a plurality of distinct wires helically wound in parallel around the inner member and at least one of the plurality of windings respectively.

3. The orifice device according to claim 2, wherein at least one of the plurality of distinct wires has a circular shape in cross-section.

4. The orifice device according to claim 2, wherein at least one of the plurality of distinct wires has a hexagonal shape in cross-section.

5. The orifice device according to claim 2, wherein at least one of the plurality of distinct wires has an octagonal shape in cross-section.

6. The orifice device according to claim 2, wherein at least one of the plurality of distinct wires has a triangular shape in cross-section.

7. The orifice device according to claim 2, wherein the plurality of distinct wires are made of a degradation-resistant material.

8. The orifice device according to claim 7, wherein the material is a nickel titanium alloy.

9. The orifice device according to claim 7, wherein the material is a stainless steel alloy.

10. The orifice device according to claim 7, wherein the material is plastic.

11. The orifice device according to claim 2, wherein the plurality of distinct wires each have a width ranging from 0.001-0.050 inches.

12. The orifice device according to claim 11, wherein the plurality of distinct wires each have a width ranging from 0.004-0.005 inches.

13. The orifice device according to claim 1, wherein the plurality of windings and the inner member define at least three separate channels for carrying one or more drugs therethrough.

14. The orifice device according to claim 13, wherein at least two of the plurality of distinct wires have a different dimension.

15. The orifice device according to claim 13, wherein at least two of the at least three separate channels deliver one or more drugs at a different fluid flow rate.

16. The orifice device according to claim 13, wherein at least two of the at least three separate channels carry a different drug.

17. The orifice device according to claim 1, wherein at least one of the at least two separate channels deliver one or more drugs at a different fluid flow rate.

18. The orifice device according to claim 1, wherein at least one of the at least two separate channels carry a different drug.

19. The orifice device according to claim 1, wherein the outer member comprises channel filling material for blocking drug flow through one of the at least two separate channels.

20. The orifice device according to claim 19, wherein the channel filling material is a glue.

21. The orifice device according to claim 1, wherein at least one of the outer member and the intermediate member is a sleeve.

22. The orifice device according to claim 1, wherein at least one of the outer member and the intermediate sleeve is made of a polymer material.

23. The orifice device according to claim 22, wherein the polymer material is PTFE.

24. The orifice device according to claim 1, wherein the plurality of windings and the inner member define four separate channels for carrying one or more drugs therethrough.

25. The orifice device according to claim 24, wherein at least one of the four separate channels deliver one or more drugs at a different fluid flow rate.

26. The orifice device according to claim 24, wherein at least one of the four separate channels carries a different drug therethrough.

27. The orifice device according to claim 24, wherein each of the four separate channels deliver one or more drugs at a different fluid flow rate.

28. The orifice device according to claim 27, wherein each of the four separate channels carries a different drug therethrough.

29. The orifice device according to claim 1, wherein the intermediate sleeve is tubular with a constant thickness from a distal end of the intermediate sleeve to a proximal end of the intermediate sleeve.

* * * * *